United States Patent
Lang et al.

(10) Patent No.: US 7,467,892 B2
(45) Date of Patent: Dec. 23, 2008

(54) CALIBRATION DEVICES AND METHODS OF USE THEREOF

(75) Inventors: Philipp Lang, Lexington, MA (US); Siau-Way Liew, Pinole, CA (US); Rene Voracek-Vargas, Sunnyvale, CA (US)

(73) Assignee: Imaging Therapeutics, Inc., Redwood City, CA (US)

( * ) Notice: Subject to any disclaimer, the term of this patent is extended or adjusted under 35 U.S.C. 154(b) by 170 days.

(21) Appl. No.: 10/917,848

(22) Filed: Aug. 12, 2004

(65) Prior Publication Data

US 2005/0078802 A1 Apr. 14, 2005

Related U.S. Application Data

(63) Continuation-in-part of application No. 10/225,363, filed on Aug. 20, 2002, which is a continuation-in-part of application No. 10/086,653, filed on Feb. 27, 2002, now Pat. No. 6,904,123, which is a continuation-in-part of application No. 09/942,528, filed on Aug. 29, 2001.

(60) Provisional application No. 60/228,591, filed on Aug. 29, 2000.

(51) Int. Cl.
*G01D 18/00* (2006.01)
(52) U.S. Cl. .............. 378/207; 378/18; 378/62
(58) Field of Classification Search .......... 378/18, 378/53, 54, 56, 207, 62; 250/252.1, 505.1
See application file for complete search history.

(56) References Cited

U.S. PATENT DOCUMENTS

| | | | | |
|---|---|---|---|---|
| 4,126,789 A | * | 11/1978 | Vogl et al. | 378/145 |
| 4,233,507 A | * | 11/1980 | Volz | 378/18 |
| 4,649,561 A | | 3/1987 | Arnold | 378/207 |
| 5,235,628 A | | 8/1993 | Kalender | 378/207 |
| 5,335,260 A | * | 8/1994 | Arnold | 378/207 |
| 5,493,601 A | | 2/1996 | Fivez et al. | 378/207 |
| 6,064,716 A | | 5/2000 | Siffert et al. | 378/53 |
| 6,178,225 B1 | | 1/2001 | Zur et al. | 378/98.2 |
| 6,289,115 B1 | | 9/2001 | Takeo | 382/130 |
| 6,320,931 B1 | | 11/2001 | Arnold | 378/56 |
| 6,694,047 B1 | | 2/2004 | Farrokhnia et al. | 382/132 |
| 6,824,309 B2 | * | 11/2004 | Robert-Coutant et al. | 378/207 |
| 2005/0010106 A1 | | 1/2005 | Lang | 600/425 |

FOREIGN PATENT DOCUMENTS

| | | |
|---|---|---|
| WO | 01/63488 | 8/2001 |
| WO | 01/65449 | 9/2001 |
| WO | WO 02/30283 A3 | 4/2002 |

(Continued)

OTHER PUBLICATIONS

Barker, R., *Case Method: Entity Relationship Modeling(Computer Aided Systems Engineering)*, 1990, Addison-Wesley Pub. Co., publisher.

(Continued)

*Primary Examiner*—Courtney Thomas
(74) *Attorney, Agent, or Firm*—Bromberg & Sunstein LLP

(57) ABSTRACT

The present invention relates to calibration devices and to methods of using these devices.

10 Claims, 5 Drawing Sheets

FOREIGN PATENT DOCUMENTS

| WO | WO 03/071934 A3 | 9/2003 |
|----|-----------------|--------|
| WO | WO 04/019256 A3 | 3/2004 |

OTHER PUBLICATIONS

Supplemental Partial European Search Report, Feb. 9, 2007.
JP 05099829 - English Abstract (1 page) Apr. 23, 1993 (Matsushita Electric Ind. Co., Ltd., Oct. 4, 1991).
JP 08186762 - English Abstract (1 page) Jul. 16, 1996 (Toshiba Medical Eng. Co. Ltd., Dec. 12, 1994).
JP 10145396 - English Abstract (*Patent Abstracts in Japan*, 1 page) May 29, 1998 (Siemens AG, Jun. 26, 1997).
JP 11069136 - English Abstract (1 page) Mar. 9, 1999 (Canon Inc., Aug. 18, 1997).
JP 11112877 - English Abstract (1 page) Apr. 23, 1999 (Fuji Photo Film Co., Ltd., Sep. 30, 1997).
JP 2000126168 - English Abstract (1 page) May 9, 2000 (Teijin Ltd., Oct. 22, 1998).
JP 2000139889 - English Abstract (1 page) May 23, 2000 (Canon, Inc., Aug. 24, 1999).

\* cited by examiner

Sacle: 2:1

| ITEM NO. | PARTY NUMBER | QTY. |
|---|---|---|
| 1 | Bottom Laminated Plastic-V01 | 1 |
| 2 | Top Laminated Plastic-V01 | 1 |
| 3 | Copper Strip-V01 | 1 |

<u>ASSEMBLY NOTES</u>

1. LAMINATE COPPER PARTS BETWEEN TWO (2) 0.012" THICK PLASTIC LAYERS AS SHOWN 0.625"+0.0005"

2"
Scale: 2:1

SCALE 2:1
Hip X-ray Aluminum
Calivration Device

Material: Alloy 2024 Precision Ground Aluminum Rod 5/8" ASTM B211/221

CALIBRATION DEVICES AND METHODS OF USE THEREOF

CROSS-REFERENCE TO RELATED APPLICATIONS

This application is a continuation-in-part of U.S. Ser. No. 10/225,363, filed Aug. 20, 2002, which is a continuation-in-part of U.S. Ser. No. 10/086,653, filed Feb. 27, 2002, now U.S. Pat. No. 6,904,123, which in turn is a continuation-in-part of U.S. Ser. No. 09/942,528, filed Aug. 29, 2001, which in turn claims the benefit of U.S. Provisional Patent Application Ser. No. 60/228,591, filed 29 Aug. 2000, all of which applications are incorporated herein by reference in its entirety.

TECHNICAL FIELD

The present invention is in the field of radiographic imaging and analysis thereof. In particular, calibration phantoms and methods of using these calibration phantoms are described.

BACKGROUND

X-rays and other radiographic analysis are important diagnostic tools. In order to rely on data extracted from radiographs, it is often helpful to include a phantom of known radiopacity. Calibration references (also known as calibration phantoms) for use in imaging technologies have also described. See, e.g., U.S. Pat. No. 5,493,601 and U.S. Pat. No. 5,235,628. U.S. Pat. No. 5,335,260 discloses a calibration phantom representative of human tissue containing variable concentrations of calcium that serves as reference for quantifying calcium, bone mass and bone mineral density in radiography and CT imaging systems. However, currently-available calibration phantoms are not always accurate, due to both the effect of structures or materials that project on or with the calibration phantom and, additionally, to the fact that one or more regions of the calibration phantom do not always appear on the x-ray image.

Thus, there remains a need for calibration devices that provide references for density and geometry of the images structures.

SUMMARY

The present invention meets these and other needs by providing compositions and methods that allow for calibration of density and/or geometry data obtained from radiographs, particularly x-rays.

In one aspect, a calibration device comprising a radiopaque material (e.g., copper or aluminum) having a stepped thickness is described. In certain embodiments, the step-wedge calibration device has equivalent bone area density coverage ranging from about 0.02 g/cm$^2$ to about 1.5 g/cm$^2$ (this range having a coefficient of variation of less than about 10%). Any of the step-wedges described herein may include one or more clear coverings on one more sides, for example a plastic laminate (e.g., approximately 0.012 inches thickness) on either side of the step-wedge.

In another aspect, a calibration device comprising a radiopaque material (e.g., copper or aluminum) in a rod-shape is described. In certain embodiments, the rod-shaped calibration device has an optical density of between about 30% and about 70% of the optical density range covered by a step-wedge as described herein, when imaged with energy between about 70 kVp and 80 kVp (this range having a coefficient of variation of less than about 10%).

In another aspect, the calibration device comprises any of the step-wedge calibration devices described herein in combination with any of the rod-shaped calibration devices described herein. The step-wedge and rod may be permanently or temporarily attached to each other, for example using a plastic laminate to align the calibration devices such that the long axis of the rod is parallel to the long axis of each rectangle making up the step-wedge.

In another aspect, methods of using any of the calibration devices described herein, alone or in combination, are described. In certain embodiments, the methods comprise obtaining an x-ray image of hip comprising one or more calibration devices as described herein. In certain embodiments, the method of obtaining a hip x-ray of a patient comprises the steps of centering the central ray to femoral neck; placing one or more calibration devices as described herein with the center label aligned with transverse line of aiming cross placing a film cassette in bucky tray; centering the film cassette to central ray; adjusting width of collimator to include all of the calibration device in exposure field; rotating the patient's leg internally 15–20 degrees; and producing an x-ray image of the patient's hip. In certain embodiments, the x-ray image is produced using a current of 150 mA, energy of 70 kV to 80 kV, using an automatic exposure time, a 400 speed screen and a source height of approximately 40 inches (102 cm). In any of the methods described herein, the film size may be 14"×11" (36 cm×28 cm). Furthermore, the leg may be held in place by the use of blocks and/or straps.

Another aspect of the invention is a kit for aiding in assessing the condition of bone in a subject, which kit comprises a software program and one or more calibration devices as described herein. When installed and executed on a computer reads an x-ray image (e.g. a digital or digitized dental x-ray) comprising the calibration device(s) and produces a computer readout showing bone mineral density and/or bone structure. Any of the kits described herein can also include an x-ray film, x-ray film holders and computer programs (e.g., software) for displaying and/or generating a bill for the readout regarding bone mineral density.

In yet another aspect, methods of diagnosing osteoporosis in a subject are provided, for example using any of the kits, methods and/or devices described herein. In certain embodiments, the methods of diagnosing osteoporosis in a subject comprise using a computer program to analyze bone mineral density and/or bone structure of an x-ray image and comparing the bone mineral density and/or bone structure data obtained from the image with a reference standard or curve, thereby determining if the subject has osteoporosis. In certain embodiments, the x-ray image includes a calibration phantom, for example a calibration phantom as described herein. In other embodiments, a reference calibration curve can be used to analyze the image.

In still further aspects, methods of assessing bone mineral density and/or bone structure are used to provide suitable treatment for a subject in need thereof. For instance, using any of the methods, kits, and/or devices described herein, the presence of osteoporosis in a subject can be diagnosed and that subject provided with appropriate therapy (e.g., one or more anti-resorptive agents and/or one or more anabolic agents).

These and other embodiments of the subject invention will readily occur to those of skill in the art in light of the disclosure herein.

BRIEF DESCRIPTION OF THE FIGURES

FIG. 1A is a top view depicting dimensions of each of the rectangles making up the step-wedge. FIG. 1B is a perspective view. FIG. 1C is side view and depicts the thickness of each rectangle making up the step-wedge.

FIG. 2A depicts positioning of the step-wedge between two plastic sheets. FIG. 2B depicts the dimensions of the plastic covering and overall device. FIG. 2C is a perspective view depicting a laminated step-wedge calibration device suitable for use in hip x-ray imaging.

DETAILED DESCRIPTION

Figure 1A:
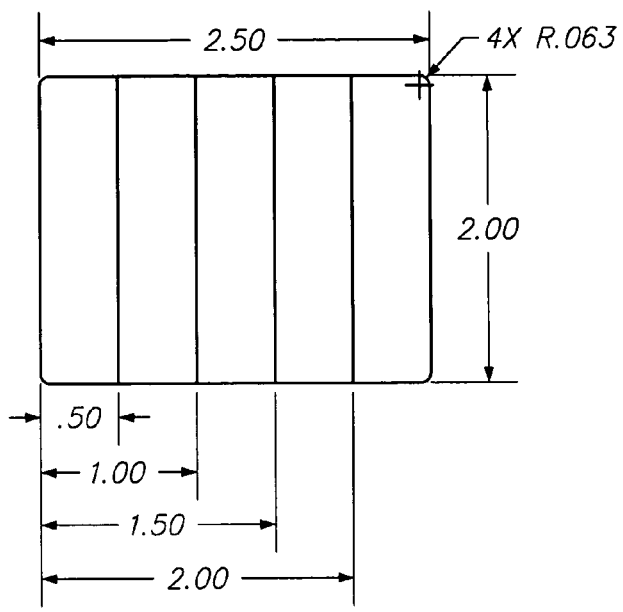
FIGS. 1A–C, depict an exemplary step-wedge calibration device of the present invention.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

As will be appreciated by those of skill in the art, methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The practice of the present invention employs, unless otherwise indicated, conventional methods of database storage and manipulation, within the skill of the art. Such techniques are explained fully in the literature. See, e.g., Numerical Mathematical Analysis, Third Edition, by J. B. Scarborough, 1955, John Hopkins Press, publisher; System Analysis and Design Methods, by Jeffrey L. Whitten, et al., Fourth Edition, 1997, Richard D. Irwin, publisher; Modern Database Management, by Fred R. McFadden, et al., Fifth Edition, 1999, Addison-Wesley Pub. Co., publisher; Modern System Analysis and Design, by Jeffery A. Hoffer, et al., Second Edition, 1998, Addison-Wesley Pub. Co., publisher; Data Processing: Fundamentals, Design, and Implementation, by David M. Kroenke, Seventh Edition, 2000, Prentice Hall, publisher; Case Method: Entity Relationship Modelling (Computer Aided Systems Engineering), by Richard Barker, 1990, Addison-Wesley Pub Co., publisher.

General Overview

Methods and compositions useful in analyzing x-ray images are described. In particular, the invention includes methods of obtaining and/or deriving information from an x-ray image in network environment. Additionally, the present invention relates to the provision of accurate calibration phantoms for X-ray systems and methods of using these calibration phantoms. Typically, the calibration phantom is formed of a material that simulates the properties of human bone tissue and is provided in an x-ray assembly such that improved accuracy and precision in the quantification of calcium, bone mass and bone density using conventional X-ray equipment is achieved.

Calibration Devices

Although a wealth of information can be obtained from radiographic images alone, it is highly preferred that the images include one or more accurate reference markers, for example calibration phantoms for assessing density and geometry of any given structure in any given image. Geometry refers broadly to any bone structure parameter, for example as described in U.S. Ser. No. 10/809,578, incorporated by reference herein in its entirety.

Thus, in certain aspects, the current invention provides for methods and devices that allow accurate quantitative assessment of information contained in an image such as density, geometry or morphology of an anatomic structure.

The calibration phantom materials and methods of the present invention are suitable for use in both conventional radiography systems and computed tomography (CT) systems. In conventional radiography systems, for example, a step-wedge phantom can be fabricated from a matrix containing a desired concentration of reference material in varying thicknesses is used. In certain embodiments, the image is an x-ray image, for example of hip, spine, knee, ankle, elbow, etc. X-ray images can be acquired using well-known techniques from any local site. For example, in certain aspects, 2D planar x-ray imaging techniques are used. 2D planar x-ray imaging is a method that generates an image by transmitting an x-ray beam through a body or structure or material and by measuring the x-ray attenuation on the other side of said body or said structure or said material. 2D planar x-ray imaging is distinguishable from cross-sectional imaging techniques such as computed tomography or magnetic resonance imaging.

X-ray images that are captured using conventional x-ray film can be digitized using any suitable scanning device. The digitized x-ray image may then transmitted over the network, e.g. the Internet, into a remote computer or server. It will be readily apparent that x-ray images can also be acquired using digital acquisition techniques, e.g. using phosphorus plate systems or selenium or silicon detector systems, the x-ray image information is already available in digital format. In this case the image can be transmitted directly over the network, e.g. the Internet, or alternatively, it can be compressed prior to transmission.

In preferred embodiments, when an x-ray of an anatomic structure or a non-living object is acquired one or more calibration devices are included in the field of view. Any suitable calibration phantom can be used, for example, one that comprises aluminum, copper and/or or other radiopaque materials. U.S. Pat. No. 5,335,260 describes other calibration phantoms suitable for use in assessing bone mineral density in x-ray images. Examples of other suitable calibration reference materials can be fluid or fluid-like materials, for example, one or more chambers filled with varying concentrations of calcium chloride or the like.

It will be readily apparent that a calibration phantom can contain several different areas of different radiopacity. For example, the calibration phantom can have a step-like design, whereby changes in local thickness of the wedge result in differences in radiopacity. Stepwedges using material of varying thickness are frequently used in radiology for quality control testing of x-ray beam properties. By varying the thickness of the steps, the intensity and spectral content of the x-ray beam in the projection image can be varied. Stepwedges are commonly made of aluminum, copper and other convenient and homogeneous materials of known x-ray attenuation properties. Stepwedge-like phantoms can also contain calcium phosphate powder or calcium phosphate powder in molten paraffin.

Figure 1B:
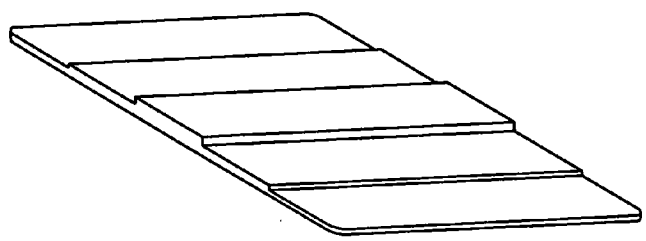
Figure 1C:
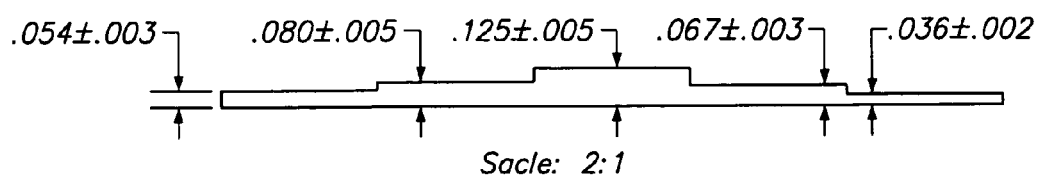

FIG. 1, panels A–C, shows an exemplary step-wedge calibration phantom according to the present invention. Dimensions are shown in inches unless other specified. Panel (A) shows a top view and the overall dimensions as well as the distance between wedges (6 wedges shown in FIG. 1). Each rectangle of the step-wedge is approximately 0.5 inch long. Panel (B) shows a perspective view and Panel (C) shows a side view and depicts dimensions of the stepped nature of the phantom. The dimensions (e.g., height) of each component of the step-wedge is shown between the arrows, in a 2:1 scale. One of skill in the art will recognize that the shape and specific dimensions of the phantom shown in FIG. 1 are exemplary (e.g., for hip x-rays) and can be varied according to the teachings herein. For instances in which the calibration phantom is to be used in smaller x-rays (e.g., dental x-rays), the device will be smaller. In one preferred embodiment, the step-wedge calibration phantom comprises copper.

Figure 2A:
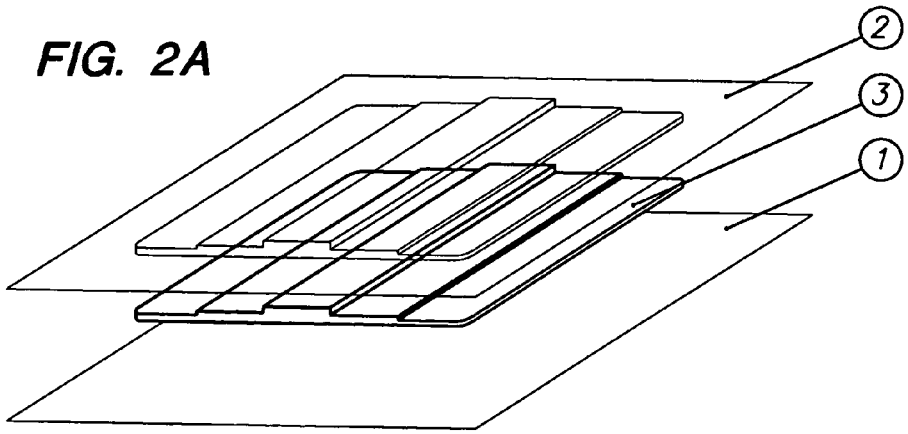
FIGS. 2A–C depict lamination of the exemplary step-wedge calibration device of FIG. 1 between two clear plastic sheets.
Figure 2B:
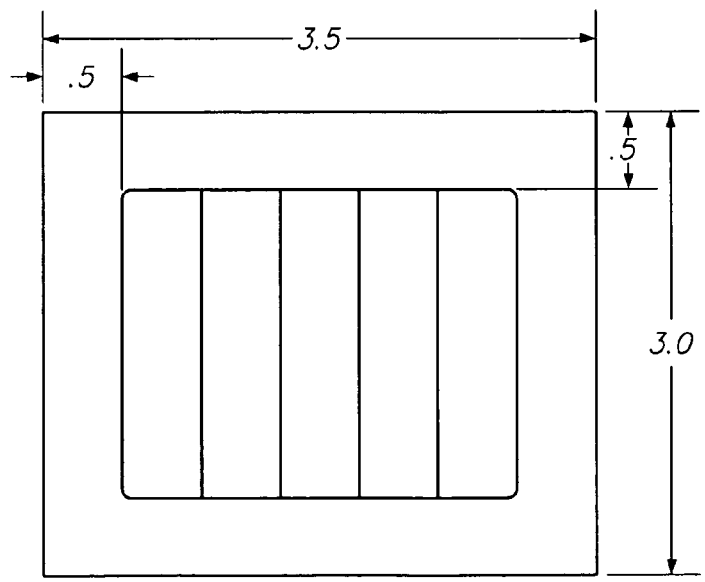
Figure 2C:
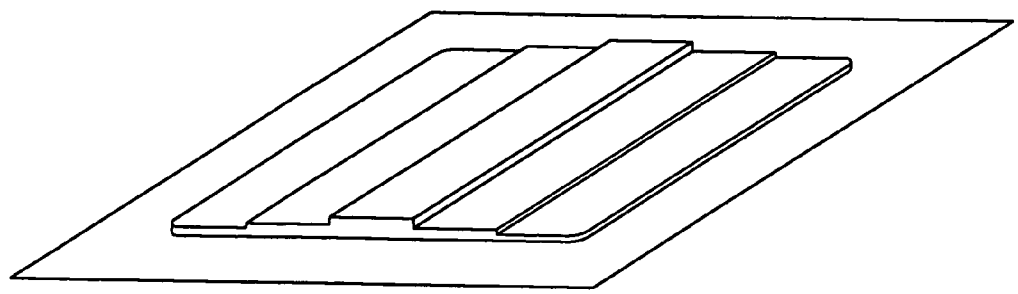

FIGS. 2A–C shows lamination of an exemplary copper step-wedge as described herein between to plastic layers. The thickness of the plastic is preferably such that it does not significantly effect imaging of the wedge. For example, as shown in FIG. 2, each plastic sheet may be approximately 0.012 inches thick.

Figure 3:
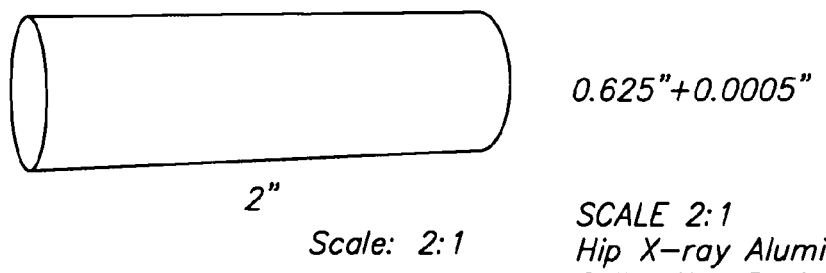
FIG. 3 is a perspective view depicting an exemplary rod-shaped calibration device.

FIG. 3 shows another exemplary embodiment of the present invention comprising a rod-shaped calibration device. The dimensions and characteristics of the exemplary device are shown in FIG. 3 and described in Example 1 below.

The calibration devices described herein may be reused and do not require sterilization prior to use. The calibration devices are typically re-useable for at least 6 months.

Figure 4:
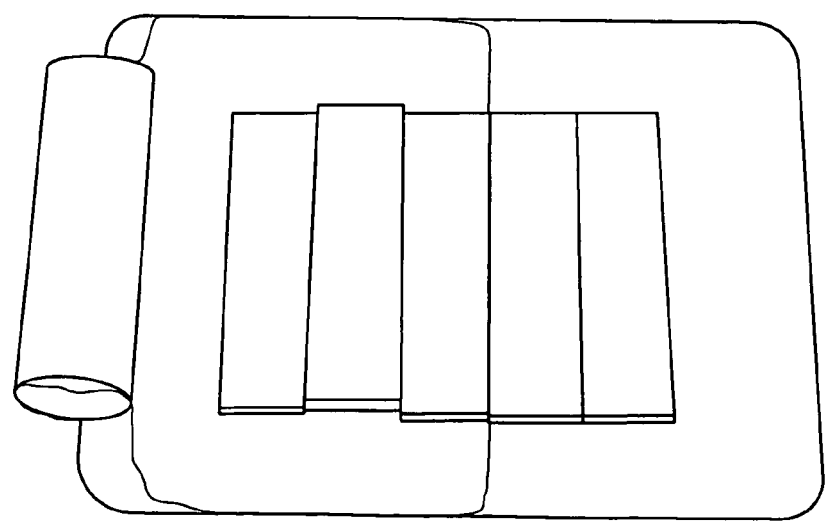
FIG. 4 is a perspective view depicting an exemplary combination calibration device as described herein comprising step-wedge and rod-shaped calibration devices.

In yet other embodiments, calibration devices as described herein may be combined to further enhance the accuracy of the data obtained from the radiograph. For example, as shown in FIG. 4, a step-wedge can be permanently attached to a rod-shaped calibration device. FIG. 4 depicts the device of FIG. 2C (laminated step-wedge) in combination with the device depicted in FIG. 3. In one preferred embodiment, the rod-shaped calibration device is affixed to the edge of the plastic laminate of the step-wedge such that the long axis of the rod is parallel to the long axis of the rectangles making up the step-wedge.

Since the density and attenuation of the calibration phantom are both known, the calibration phantom provides an external reference for measuring the density of the anatomic structure or non-living object to be measured.

Preferably, the calibration phantom can be imaged at the same time as the x-ray image. The calibration phantom can be physically connected to an x-ray film and/or film holder. Such physical connection can be achieved using any suitable mechanical or other attachment mechanism, including but not limited to adhesive, a chemical bond, use of screws or nails, welding, a Velcro™ strap or Velcro™ material and the like. Similarly, a calibration phantom can be physically connected to a detector system or a storage plate for digital x-ray imaging using one or more attachment mechanisms (e.g., a mechanical connection device, a Velcro™ strap or other Velcro™ material, a chemical bond, use of screws or nails, welding and an adhesive).

The attachment may be permanent or temporary and the calibration phantom can be integral (e.g., built-in) to the film, film holder and/or detector system or can be attached or positioned permanently or temporarily appropriately after the film and/or film holder is produced, whether integrally formed or not. Thus, the calibration phantom can be designed for single-use (e.g., disposable) or for multiple uses with different x-ray images. Thus, in certain embodiments, the calibration phantom is reusable and, additionally, can be sterilized between uses. Integration of a calibration phantom can be achieved by including a material of known x-ray density between two of the physical layers of the x-ray film. Integration can also be achieved by including a material of known x-ray density within one of the physical layers of the x-ray film. Additionally, the calibration phantom can be integrated into the film cover. A calibration phantom or an external standard can also be integrated into a detector system or a storage plate for digital x-ray imaging. For example, integration can be achieved by including a material of known x-ray density between two of the physical layers of the detector system or the storage plate. Integration can also be achieved by including a material of know x-ray density within one of the physical layers of the detector system or the storage plate.

In certain embodiments, for example those embodiments in which the calibration phantom is temporarily attached to the x-ray assembly, cross-hairs, lines or other markers may be placed on the apparatus as indicators for positioning of the calibration phantom. These indicators can help to ensure that the calibration phantom is positioned such that it doesn't project on materials that will alter the apparent density in the resulting image.

Methods

Any of the calibration phantom-containing assemblies described herein can be used in methods of analyzing and/or quantifying density and/or geometry of a structure in an x-ray image. The methods generally involve simultaneously imaging or scanning the calibration phantom and another material (e.g., bone tissue from a subject) for the purpose of quantifying the density or geometry of the imaged material (e.g., bone mass).

Thus, under the method of the present invention, a calibration phantom is preferably imaged or scanned simultaneously with the individual subject, although the invention allows for non-simultaneous scanning of the phantom and the subject. Methods of scanning and imaging structures by radiographic technique are well known. By placing the calibration phantom in the x-ray beam with the subject, reference calibration samples allow corrections and calibration of the absorption properties of bone. When the phantom is imaged or scanned simultaneously with each subject, the variation in x-ray beam energy and beam hardening are corrected since the phantom and the subject both see the same x-ray beam spectrum. Each subject, having a different size, thickness, muscle-to-fat ratio, and bone content, attenuate the beam differently and thus change the effective x-ray beam spectrum. It is necessary that the bone-equivalent calibration phantom be present in the same beam spectrum as the subject's bone to allow accurate calibration.

Figure 5A:
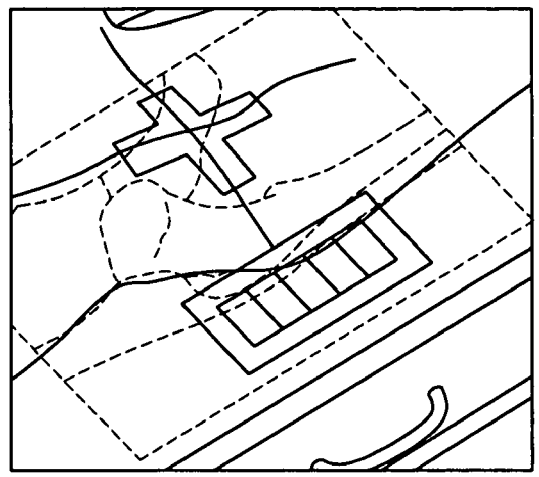
FIGS. 5A and B depict alignment of the bone, film and calibration device.
Figure 5B:
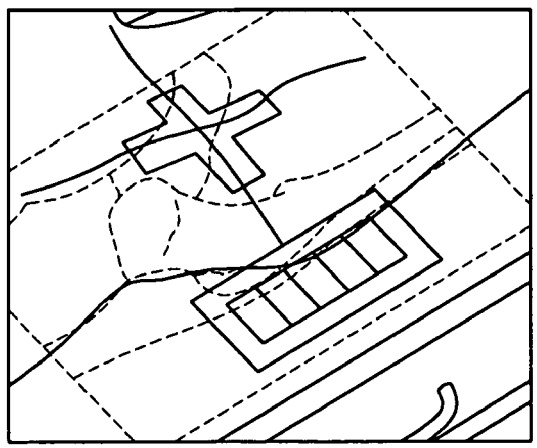
FIG. 5, panels A–C, depict selected steps in producing an x-ray image including a calibration device as described herein of a patient's hip.
FIG. 5C depicts positioning of the patient's leg and production of the x-ray image.
Figure 5C:
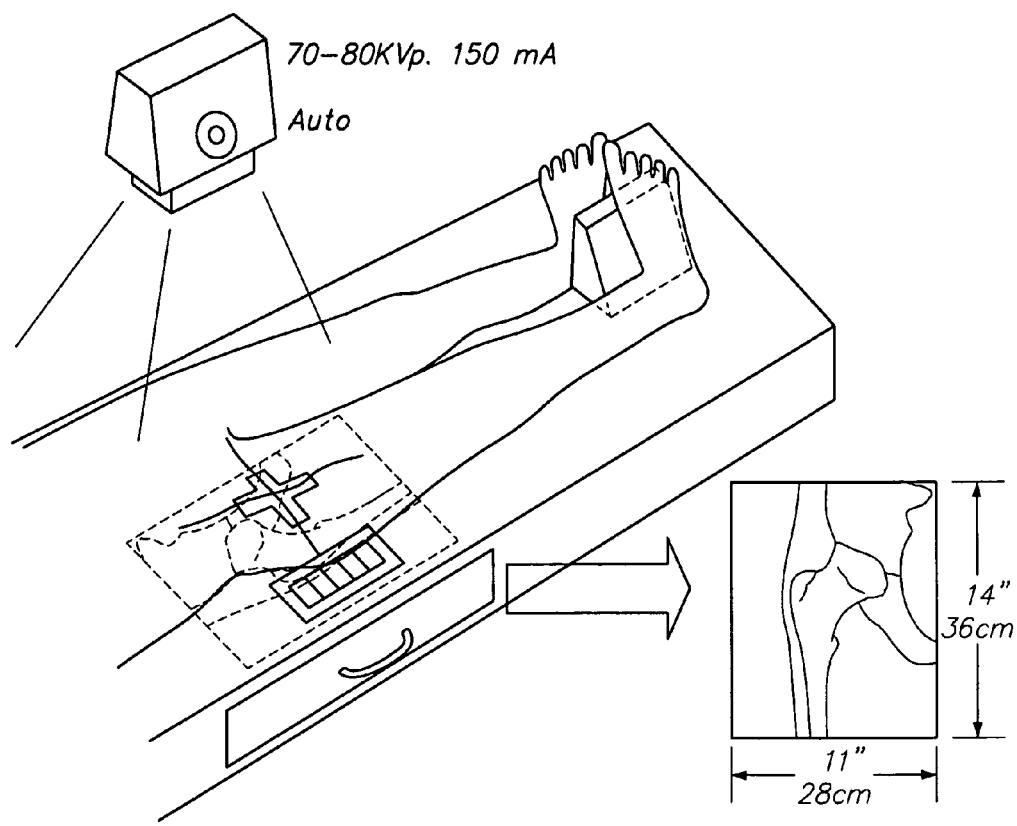

FIGS. 5A–C depict an exemplary method of using a calibration phantom as described herein to produce an x-ray image. FIG. 5A shows alignment of the central ray with the femoral neck (top arrow) as well as alignment of the center of the calibration device along the transverse line of aiming cross (bottom arrow). FIG. 5B depicts placement of a film cassette in a bucky tray and the film centered to central ray and adjusted width of collimator to include all of calibration device in exposure field. As shown in FIG. 5C, the x-ray is then taken after the patient's leg has been rotated 15–20 degrees internally and held in the rotated position. Exemplary x-ray conditions and parameters are also shown in FIG. 5C and described in Example 2 below.

In addition, the data obtained from the calibration device(s) (e.g., density and/or geometry) can be further manipulated. For example, one or more calibration curves can be constructed as described for example in International Publications WO 02/30283; WO 03/071934 and WO 04/019256, which disclosures are incorporated herein in their entireties.

Kits

The invention also provides kits for obtaining information from x-ray images, for example for obtaining information regarding bone mineral density from an x-ray. In certain embodiments, the kit comprises one or more computer (e.g., software) programs, for example for receiving, analyzing and generating reports based on x-ray images. In further embodiments, the kits can include calibration phantoms, for example calibration phantoms integrated or attachable-to x-ray film and/or x-ray film holders.

All of these aspects of the invention can be practiced separately or in combination. Typically, the use of combinations of the embodiments listed above is more advantageous. Further, although preferred embodiments of the subject invention have been described in some detail, it is understood that obvious variations can be made without departing from the spirit and the scope of the invention.

EXPERIMENTAL

Below are examples of specific embodiments for carrying out the present invention. The examples are offered for illustrative purposes only, and are not intended to limit the scope of the present invention in any way.

Example 1

Calibration Devices

A. Copper Stepped-Wedge

A step-wedge comprising copper was made as shown in FIG. 1. Dimensions of the step-wedge are shown in FIGS. 1 and 2. The device had equivalent area bone density coverage range of 0.02 g/cm$^2$ to 1.5 g/cm$^2$ and this bone density measurement had a variation of less than 10%. The step-wedge was laminated in plastic.

B. Aluminum Calibration Device

A calibration device made of aluminum was constructed as follows. Aluminum was selected because it has an x-ray attenuation coefficient similar to that of human cortical bone. A rod-shaped aluminum calibration device having the dimensions shown in FIG. 3 was constructed using standard techniques.

The aluminum device had an optical density between about 30% to 70% when imaged with energy between 70 kVp to 80 kVp. This optical density measurement had a coefficient of variation of less than 10%.

C. Combination Devices

The copper step-wedge and aluminum rod described above were combined into a single calibration device as follows. Using clear plastic sheets the aluminum rod was attached to the previously-laminated step-wedge such that the long axis of the aluminum rod was essentially parallel to the rectangles making up the step-wedge. FIG. 4.

Since the x-ray attenuation coefficient of copper decreases more rapidly with higher x-ray energy than that of aluminum, the x-ray energy used to capture an image can be estimated by comparing the optical density of the aluminum device to that of the copper device.

By providing a mechanism to estimate the x-ray energy, a more accurate attenuation coefficient of the copper calibration device is used to generate a more accurate standard calibration curve adjusted for the x-ray energy.

Example 2

Use of Calibration Device in Hip X-Rays

A calibration device as described in Example 1 (copper step-wedge or combination copper step-wedge-aluminum calibration device) was placed on the x-ray table, lengthwise, lateral, and adjacent to the patient with center of device aligned with the transverse aiming cross of collimator light. The central ray was centered with respect to the femoral neck and the calibration device was placed with the center is aligned with the transverse line of aiming cross. (FIG. 5A).

Subsequently, the film cassette was placed in the busky tray and centered to the central ray. The width of the collimator was adjusted to include all of the calibration device in the exposure field. (FIG. 5B). The patient's leg was then rotated internally 15–20 degrees using foam block and Velcro to maintain positioning. (FIG. 5C)

An x-ray image was created using the following parameters:

| | |
|---|---|
| Current | 150 mA |
| Energy | 70 kV–80 kV |
| Exposure time | Auto |
| Film size | 14" × 11" (36 cm × 28 cm) |
| Screen | 400 speed |
| Source height | 40" (102 cm) |

For images including the combination device, the x-ray energy used to capture an image was estimated by comparing the optical density of the aluminum device to that of the copper device.

The instant invention is shown and described herein in what is considered to be the most practical, and preferred embodiments. It is recognized, however, that departures may be made there from, which are within the scope of the invention, and that obvious modifications will occur to one skilled in the art upon reading this disclosure.

The invention claimed is:

1. A method of analyzing an x-ray, the method comprising the steps of:
  generating a radiographic image comprising at least one calibration phantom, the at least one calibration phantom including a first material and a second material, the first material having an x-ray attenuation coefficient that decreases more rapidly with higher x-ray energy than the second material;
  comparing the optical density of the first and second material in the image; and estimating at least one image acquisition parameter based on the comparison.

2. The method of claim 1, wherein the x-ray image is of a patient's hip and the x-ray is generated by:
- centering the central ray to the femoral neck;
- placing the at least one calibration phantoms with the center label aligned with a transverse line of aiming cross
- placing a film cassette in a bucky tray;
- centering the film cassette to the central ray;
- adjusting the width of the collimator to include all of the calibration device in the exposure field;
- rotating the patient's leg internally 15–20 degrees; and
- producing an x-ray image of the patient's hip.

3. The method of claim 2, wherein the x-ray image is produced using a current of 150 mA, energy of 70 kV to 80 kV, using an automatic exposure time, a 400 speed screen and a source height of approximately 40 inches (102 cm).

4. The method according to claim 1, wherein the at least one image acquisition parameter estimated is the x-ray energy used to capture the image.

5. The method according to claim 4, further comprising determining a calibration curve adjusted for the estimated x-ray energy.

6. The method according to claim 1, wherein the first material is copper and the second material is aluminum.

7. The method according to claim 1, wherein the at least one calibration phantom includes a radioopaque step-wedge and a radioopaque rod.

8. The method according to claim 7, wherein the step-wedge includes rectangular steps having a long axis, wherein the rod has a long axis, and wherein the long axis of the rod and the rectangular steps are parallel.

9. The method according to claim 1, wherein the image further includes bone, the method further comprising deriving information on density or structure of bone from the image using the at least one calibration phantom.

10. A method of analyzing an x-ray, the method comprising:
- generating a radiographic image comprising at least one calibration phantom; and
- estimating at least one image acquisition parameter of the image based, at least in part, on the calibration phantom, wherein the at least one image acquisition parameter includes imaging geometry.

* * * * *

UNITED STATES PATENT AND TRADEMARK OFFICE
CERTIFICATE OF CORRECTION

PATENT NO. : 7,467,892 B2  
APPLICATION NO. : 10/917848  
DATED : December 23, 2008  
INVENTOR(S) : Philipp Lang et al.

Page 1 of 1

It is certified that error appears in the above-identified patent and that said Letters Patent is hereby corrected as shown below:

In Col. 9, line 6  
replace "phantoms"  
with --phantom--

Signed and Sealed this

Seventeenth Day of February, 2009

JOHN DOLL  
*Acting Director of the United States Patent and Trademark Office*